United States Patent
Burkhart et al.

(10) Patent No.: US 7,326,420 B2
(45) Date of Patent: Feb. 5, 2008

(54) BENZOYL PEROXIDE COMPOSITIONS HAVING INCREASED POTENCY

(76) Inventors: Craig G. Burkhart, 4556 Crossfields Rd., Toledo, OH (US) 43623; Craig N. Burkhart, 4556 Crossfields Rd., Toledo, OH (US) 43623

( * ) Notice: Subject to any disclaimer, the term of this patent is extended or adjusted under 35 U.S.C. 154(b) by 283 days.

(21) Appl. No.: 10/917,240

(22) Filed: Aug. 12, 2004

(65) Prior Publication Data

US 2005/0256200 A1    Nov. 17, 2005

Related U.S. Application Data

(63) Continuation-in-part of application No. 10/847,906, filed on May 18, 2004, which is a continuation of application No. 10/091,607, filed on Mar. 6, 2002, now Pat. No. 6,737,070.

(60) Provisional application No. 60/588,702, filed on Jul. 17, 2004, provisional application No. 60/494,403, filed on Aug. 12, 2003, provisional application No. 60/273,787, filed on Mar. 6, 2001.

(51) Int. Cl.
*A61K 8/02* (2006.01)
*A61K 33/40* (2006.01)
*A61K 33/26* (2006.01)

(52) U.S. Cl. ............ 424/400; 424/401; 424/613; 424/646; 514/859; 514/871; 514/946; 514/947

(58) Field of Classification Search ........... 424/400, 424/401, 613, 646, 65; 514/859, 871, 946, 514/947
See application file for complete search history.

(56) References Cited

U.S. PATENT DOCUMENTS

| | | | |
|---|---|---|---|
| 4,895,727 A * | 1/1990 | Allen | 424/642 |
| 5,446,028 A | 8/1995 | Klein et al. | |
| 5,767,098 A | 6/1998 | Klein et al. | |
| 6,013,637 A | 1/2000 | Klein et al. | |
| 6,737,070 B1 * | 5/2004 | Burkhart | 424/401 |

OTHER PUBLICATIONS

Warner, Gregory T. and Plosker, Greg L.; "Clindamycin/Benzoyl Peroxide Gel A Review of its Use in the Management of Acne", American Journal of Clinical Dermatologists 2002 3 (5) pp. 351-353.

* cited by examiner

*Primary Examiner*—Shelley A. Dodson
(74) *Attorney, Agent, or Firm*—MacMillan, Sobanski & Todd, LLC

(57) ABSTRACT

A benzoyl peroxide composition having increased potency includes benzoyl peroxide, a tertiary amine and/or a transition metal, and a base that increases radicals formed by the peroxide.

20 Claims, No Drawings

BENZOYL PEROXIDE COMPOSITIONS HAVING INCREASED POTENCY

CROSS-REFERENCE TO RELATED APPLICATIONS

This application is a continuation-in-part of pending U.S. application Ser. No. 10/847,906, filed May 18, 2004, which is a continuation of U.S. application Ser. No. 10/091,607, filed Mar. 6, 2002, now U.S. Pat. No. 6,737,070, issued May 18, 2004, which claimed the benefit of U.S. provisional application Ser. No. 60/273,787, filed Mar. 6, 2001. This application claims the benefit of U.S. provisional application Ser. No. 60/494,403, filed Aug. 12, 2003, and U.S. provisional application Ser. No. 60/588,702, filed Jul. 17, 2004.

BACKGROUND OF THE INVENTION

This invention relates in general to methods of treating skin conditions such as acne, and in particular to methods of increasing the efficacy of peroxides such as benzoyl peroxide in the treatment of skin conditions.

The pathophysiology of acne vulgaris, the most common cutaneous disease, is the consequence of the interplay of follicular hyperkeratinization, bacteria in the follicular canal, and sebum production. The exact mechanism triggering the development of the comedone and the stimuli causing the non-inflamed lesion to become provoked are poorly understood. The microbiology of acne vulgaris and its immunologic ramifications constitute a major thrust of present research in the elucidation of the pathogenesis of inflammatory acne. Within the microbial flora of the pilosebaceous unit, *P. acnes* is the most meaningful organism in acne causation.

The methods of acne therapy are usually grouped into several categories such as keratolytics, antibacterials, sebosuppressives, and hormones. Benzoyl peroxide (BP) is the most widely used topical agent for acne since its introduction in the 1960's. BP is very effective for the treatment of acne because it is antibacterial, functions as a peeling agent, has comedolytic activity, and reduces free fatty acid levels. Concomitant topical treatment of BP and erythromycin is stated to be superior to BP alone. However, no synergistic activity has been found with this combination. Instead, such combination therapies are hypothesized to gain their efficacy by the coupled action of two effective treatments.

SUMMARY OF THE INVENTION

This invention relates to methods of increasing the efficacy of peroxides such as benzoyl peroxide in the treatment of skin conditions such as acne. In a preferred embodiment, the invention relates to methods of increasing radicals formed by peroxides on/in the skin, more specifically near/in the comedone, for topical use in dermatology.

In a specific embodiment, the invention relates to the use of transitional metals such as Cu(1) and ferrous ions to increase the efficacy of peroxides such as benzoyl peroxide.

In another embodiment, the invention relates to a method by which a peroxide such as benzoyl peroxide and its activator (or adjunctive agent) are added to the skin surface at the same time (and not days or months before). This ensures that the ingredients are not inactivated or lost strength by being placed together prior to usage.

In another embodiment, the invention relates to the use of a more soluble form of peroxide such as benzoyl peroxide to increase its efficacy.

In another embodiment, the invention relates to the addition of a side chain to a peroxide such as benzoyl peroxide so that it is activated by light.

In a further embodiment, the invention relates to the addition of a tertiary amine to a peroxide such as benzoyl peroxide at the time of skin application, to improve the efficacy of the peroxide. This could include any tertiary amine structure except for an erythromycin structure.

In another embodiment, the invention relates to the addition of dapsone or other material to a peroxide such as benzoyl peroxide to improve its efficacy.

Various advantages of this invention will become apparent to those skilled in the art from the following detailed description of the preferred embodiments.

DETAILED DESCRIPTION OF THE PREFERRED EMBODIMENTS

This invention relates to methods of increasing the efficacy of peroxides such as benzoyl peroxide in the treatment of skin conditions such as acne. In a preferred embodiment, the invention relates to methods of increasing radicals formed by peroxides on/in the skin, more specifically near/in the comedone (but not limited thereto), for topical use in dermatology. The methods use the radicals formed by peroxides such as benzoyl peroxide, optimizing conditions such that the skin/comedone is the only place they are formed as opposed to in a storage container or wherever the benzoyl peroxide happens to be from the time of application to when the benzoyl peroxide breaks down into its radicals or is metabolized).

The methods of the invention may use the principles of photodynamic therapy directed at acne. Instead of forming radicals in cancer cells, the methods form radicals in/by the comedone (skin surface, sebum within *P. acnes*). Location and timing of formation of radicals is a very important part of the methods.

The methods use the assumption that radicals derived from BP or other peroxides are the most useful in acne therapy (as opposed to reactive oxygen intermediates used in photodynamic therapy).

In a specific embodiment, the invention relates to the use of transitional metals such as Cu(1) and ferrous ions to increase the efficacy of peroxides such as benzoyl peroxide. The use of transitional metals such as Cu(1) and ferrous ions (as alluded to in the text) to increase the efficacy of benzoyl peroxide. It is anticipated that such an addition to benzoyl peroxide would increase the generation of benzoyloxyl radicals.

The transitional metals include all the elements between Group IIA and IIIa in the periodic table. The list includes zinc, cadmium, mercury, scandium, titanium, vanadium, chromium, manganese, yttrium, zirconium, niobium, molybdenum, technetium, ruthenium, rhodium, palladium, silver, lanthanum, hafnium, tantalum, tungsten, rhenium, osmium, iridium, platinum, gold, mercury, actinium, unnilquadium, unnilpentium, unnilhexium, and uniseptium.

A few characteristics of transitional metals include:

most are harder and more brittle with higher melting points, boiling points, and heats of vaporization than the non-transitional metals.

their ions and compounds are usually colored.

they form many complex ions.

most exhibit multiple oxidation states.

many of them are paramagnetic, as are many of their compounds.

many of the metals and associated compounds are effective catalysts.

In another embodiment, the invention relates to a method by which a peroxide such as benzoyl peroxide and its activator (or adjunctive agent) are added to the skin surface at the same time (and not days or months before). An example of such would be a better package system in which the various ingredients that would be added to benzoyl peroxide would be put into a dispenser with two or three chamber (depending upon the number of items combined) to separate the product's ingredients so they do not interact until the instant you apply them to one's acne. This separation would ensure that the ingredients are not inactivated or lost strength by being placed together prior to usage.

Another example of such a system would be benzoyl peroxide (bp) dissolved in a hydrophobic solvent and the activator in a polar solvent. The BP and activator wouldn't meet until applied onto the skin surface. Lipophilic carriers are well known in the art. For an example of the activator in a hydrophilic solvent, both protic and aprotic solvents are included. Protic solvents such as methanol, ethanol, formamide, N-methylformamide, and water, a hydrogen is attached to the electronegative part of the reagent. The hydrogen has a proton-like character and strongly reacts with anionic nucleophiles. Aprotic solvents do not contain positively polarized hydrogens. These include acetone, acetonnitrile, N,N-dimethylformamide, DMSO, hexamaethylphophoric triamide—the aprotic solvents increase the reactivity of nucleophiles in SN2 reactions (the possible mechanism of radical formation by the BP tertiary amine combination).

Retin A micro is an example of a product released by a polymer. The retin A is stored in a small polymer bead. After application of these beads onto the skin, retin A slowly diffuses out of the polymer and into the skin. The invention would have the activator of benzoyl peroxide radical formation contained in a similar polymer. The activator would be slowly released (by diffusion or breakdown of the polymer) into the skin allowing it to react with BP. Alternatively, the BP could be stored in and released from the polymer. Or, both the activator and BP could be released from their own individual polymers to react when the meet (in the environment of the skin/comedone).

In another embodiment, the invention relates to the use of a more soluble form of peroxide such as benzoyl peroxide to increase its efficacy. The use of a more soluble form of benzoyl peroxide. The present-day products actually use benzoyl peroxide in the form of crystals. We are able to solubilize benzoyl peroxide either by altering its hydric solvents, or by adding a side chain to its structure.

In another embodiment, the invention relates to the addition of a side chain to a peroxide such as benzoyl peroxide so that it is activated by light. We could also add a side chain to benzoyl peroxide so that it is activated by light.

In a further embodiment, the invention relates to the addition of a tertiary amine to a peroxide such as benzoyl peroxide at the time of skin application, to improve the efficacy of the peroxide. This could include any tertiary amine structure except for an erythromycin structure. We believe that benzoyl peroxide efficacy can be improved by adding a tertiary amine at the time of skin application. Therefore, we would be including all substances (and chemicals) which have a tertiary amine within the provisional patent, be they antibiotics or whatever. The invention would include all tertiary amine structures, save for the erythromycin structure that is presently used in a commercial product named benzymycin.

Some nonlimiting examples of tertiary amines include Alfuzosin, Alimemazine, Analgesic drug (Reference 97), Atropine, alpha,alpha-bis [3-(N-benzyl-N-methyl-carbamoyl)-piperidino]-p-xylene dihydrobromide, Bupivacaine, cis-trans-Cavinton, Cloperastine, Cyamemeazine, Cyclopentolate, 2-(4,5-dihydro-1H-imidazol-2-yl)-2-propyl-1,2,3, 4-tetrahydropyrrolo]3,2,1-hi[-indole, 1-decyl-3-(N,N-diethylcarbamoyl) piperidine hydrobromide, Diltiazem, Dimethindene, Diperodone, Disopyramide, Disopyamide, semipreparative, Dixyrazine, Doxazosin, Dropropizine, Hydroxychloroquine and metabolites, Ketoconazole, Laudanosine, Marcaine, Medetomidine, Mepivacaine, Mepivacaine (micro column), Meptazinol, Methadon, Nefopam, Nicotine, Omeprazole, Oxybutynin, Oxyphencyclimide, Pheniramine, 3-PPP, Procyclidine, Promethazine, Proxyphylline, Remoxipride, Tetrahydrozoline, Tetramisole, Tetramisole (micro column), Thioridazine ring-sulphoxide, Tolperisone, Trihexyphenidyl, Trimipramine, Tropicamide, Vamicamide, Verapamil, and Vinca alcaloids. The structures and other characteristics of these tertiary amines can be found on the internet at www.chromtech.se/tertiary.htm. The listed amines are all drugs, but the methods of the invention are not limited to just drugs—any tertiary amine would work.

Along with transition metals, tertiary amines potentiate radical formation by BP. A possible mechanism involves reaction of the amine and BP by a $S_N2$ mechanism. The intermediate thus formed thermally decomposes to benzoyloxy radicals and an amine radical cation. The benzoyloxy radicals may further decompose into phenyl radicals. All of these radicals can react with biological molecules possibly causing some biological effect.

In another embodiment, the invention relates to the addition of dapsone to a peroxide such as benzoyl peroxide to improve its efficacy. Heme is a protoporphyrin. P. acnes actually produces protoporphyrins. 5-aminolevulinic acid (ALA) increases protoporphyrin production by P. acnes. ALA is the same stuff used in photodynamic chemotherapy and photodynamic antimicrobial chemotherapy. Methylene blue, toluidine blue O, phthalocyanine, and haematoporphyrin derivative could also be used. Phenothiazinium dyes could also be used. These materials might work by depleting the antioxidant levels in/around the comedone allowing the BP derived radicals to reach the comedone or spread further throughout the comedone.

Viagra (sildenafil) increases NO production by blood vessels (and maybe the skin). It is an example of a molecule inducing the skin to produce a benzoyl peroxide activator.

Testing and Discussion:

Objective: The purpose was to compare radical activity of BP alone and with various antibiotics to determine whether BP and antibiotics may be chemically synergistic.

Methods: Polymerization of tetra ethylene glycol dimethacrylate was used as a test of BP radical activity. Solutions of BP, antibiotics, and BP and antibiotics were made at 3% w/w in tetraethylene glycol dimethacrylate. All of the antibiotics except erythromycin (ERY) were obtained from prescription pills, which were crushed in a crucible. The portion of the pills that disolved in tetraethylene glycol dimethacrylate were used in the experiment. ERY was obtained in powdered form from Benzamycin® acne treatments. Aliquots of ten drops of these solutions were placed in an eight well plastic plate. The samples were heated in an oven that maintained a temperature range between 90 to 100 degrees Celsius. After various amounts of time the samples were taken out of the oven and tested for gel formation.

Polymerization of tetraethylene glycol dimethacrylate was detected visually by swirling a spatula in the solutions. Gelling constituted an indicator of BP radical activity.

Results: The results suggest that radical activity increases upon addition of certain antibiotics, such as erythromycin, to a solution of BP. ERY, minocycline (Vectrin®), and levofloxacin (Levaquin®) in combination with BP caused the tetraethylene glycol dimethacrylate to polymerize the fastest. This is assumed to be due to elevated BP radical formation. Agents that did not augment BP radical activity included doxycycline (Monodox®), and trovofloxacin (Trovan®). Upon storage in a dark room at room temperature, the ERY-BP combination gelled within an hour. The Vectrin®-BP, Diflucan®-BP, Trovan®-BP, Monodox®-BP, and Levaquin®-BP combinations did not gel within six hours. Zithromycin® (a prescription drug containing a macrolide similar to ERY) in combination with BP also gelled within an hour when stored in a dark room at room temperature. Furthermore, Zithromycin®-BP and ERY®-BP solutions gelled within an hour when stored in a refrigerator. Zithromycin® has not been tested yet at higher temperatures.

Discussion: BP induces a variety of biological effects. BP can inhibit metabolic cooperation, alter protein synthesis, induce ornithine decarboxylase activity, cause DNA strand breaks, suppress DNA synthesis, and may interfere with mitochondrial respiration. Several of these effects, such as DNA strand breaks, may be caused by BP-derived radicals. Thus, acne treatments that increase the radical activity of BP may be more effective.

Tertiary amines potentiate radical formation by BP. A possible mechanism involves reaction of the amine and BP by a $S_N2$ mechanism. The intermediate thus formed thermally decomposes to benzoyloxy radicals and an amine radical cation. The benzoyloxy radicals may further decompose into phenyl radicals. All of these radicals can react with biological molecules possibly causing some biological effect. Of the antibiotics tested, ERY, doxycycline (Monodox®), minocycline (Vectrin®), levofloxacin (Levaquin®), and trovofloxacin (Trovan®) contain tertiary amines. ERY-BP, Levaquin®-BP, and Vectrin®-BP combinations all behaved as would be expected as they demonstrated faster kinetics for radical formation than BP alone.

Contaminants and solubility may have caused the unexpected results from the Monodox®-BP and Trovan®-BP combinations. The extra chemicals contained in the pills may have dissolved in the tetraethylene glycol dimethacrylate and acted as plastisizers or radical scavengers, thus, hiding any enhanced radical formation by the antibiotic-BP combination. On the other hand, the contaminants may have accelerated the formation of BP-derived radicals. The contaminants may have affected the results for the Levaquin®-BP and Vectrin®-BP combinations as well. Furthermore, some of the antibiotics may not have dissolved in the tetraethylene glycol dimethacrylate, thus, preventing them from being involved in the experiment as only dissolved material was transferred to the plastic plate for testing.

The most impressive result was the speed that the ERY-BP and Zithromycin®-BP solutions gelled at room temperature and below. The speed of reaction between the macrolides and BP insinuates that all the BP in Benzamycin® may be completely depleted by the time a patient picks up his/her prescription to the time it is applied to his/her body. As Benzamycin® is a very effective drug for the treatment of acne, a novel drug may be formed as a product of reactions of BP and ERY with each other and/or other components in Benzamycin® that is very effective against acne. Finding this chemical may result in the discovery of improved acne treatments that do not require BP. As Zithromycin® similarly increased BP radical formation, it is probable that many macrolides mixed with BP are effective drugs for the treatment of acne.

It may be true that the BP is protected from ERY while stored in its container. For example, much of BP is in a less reactive crystalline form while in acne creams, where as it was fully dissolved in these experiments. Upon application to the skin these crystals of BP may dissolve and react with ERY producing radicals. Depending on where these radicals are formed DNA strand breaks, lipid peroxidation, or other effects may occur.

Conclusion: Radical activity of BP in tetraetylene glycol dimethacrylate is increased when tested in consort with several antibiotics, such as the macrolides. We propose that the tertiary amines contained on certain antibiotics are responsible for catalysis of BP radical formation. If increased radical formation correlates with enhanced biological effect, then these data reveal the possibility of biological synergism in mixtures of BP and antibiotics. An understanding of the mechanism of catalysis of BP radical formation by antibiotics may lead to the discovery of improved treatments for acne.

Making Benzoyl Peroxide a More Potent Treatment Modality for Numerous Skin Conditions Benzoyl peroxide (bp) has been available for over-the-counter and prescription use for several dermatologic states especially acne for over 3 decades. Our U.S. Pat. No. 6,737,070, issued May 18, 2004, explains benzoyl peroxide free radicals and the chemical action of bp with a tertiary amine or any chemical with a nitrogen molecule or any agent which excites the oxygen double bond in bp. Of note, the radicals are formed both off the bp molecule and the molecule which excites the double oxygens in bp (such as the tertiary amine in this case erythromycin, terbinafine and butenafine).

In the present invention, we make bp as potent as possible to better remedy several skin conditions. This will allow bp to react more with skin cells, abnormal cells in the epidermis, bacteria, fungus, virus, and any other abnormal development or critter within the epidermis. Moreover, by accomplishing this, we will have a quicker response and more penetration into the hair unit (in the case of acne), and into the basal cells (in the case of actinic keratoses) and into the nails (in the case of onychomycosis). We will complete this task by improving the base, using the product with agents which improve the radical formation, and/or by enhancing the permeability of the product both past the stratum corneum (the dead outer epidermal layer) to the basal layer (in the case of, for example, actinic keratoses and skin aging) and/or into the hair follicle unit (in the case of acne).

In terms of other chemicals which may excite bp, this invention would include all chemicals which might excite the bp molecule to form radicals. It would not eliminate the use of erythromycin from the list of activators. We have progressed the knowledge of this specific interaction. Moreover, the present invention makes bp more potent by methods and a system which involves more than the simple mixing of two chemicals.

The present invention is for a list of all possible disease and cosmetic states including (but not limited to): all forms of acne and related conditions (rosacea, inflammatory, comedonal, perioral dermatitis, etc.), actinic keratosis, scars, fungal and yeast infections, tinea versicolor, bacterial infections, skin aging, viral infections of the skin, eczema, psoriasis, seborrheic dermatitis, dandriff, lichen planus, sexually transmitted diseases (especially in the prevention), warts, molluscum, skin ulcerations, mouth lesions, benign and premalignant skin tumors, nail infections, and for cleansing the skin and/or hair, or as a cream or any form of topical body application. For example, this method of use of bp may be helpful against methicillin-resistant *S. aureus*, vancomycin-resistant *enterococcus*, and *pseudomonas*. This invention is for application for both human and animal usage.

In the case of acne (as an example), our product could be compared with present formulations of benzoyl peroxide and erythromycin. Past science suggests that the synergy is merely having two antibiotics mixed together. Our work in this area, has shown that there is a chemical reaction. Now, we want to maximize this reaction. In comparison to the present benzamycin (acne) product (as an example), we should eventually be able to show that our product:
will act as a more significant pealing agent.
will have more comedolytic properties
will have more antibacterial properties
will have increased penetration
will more significantly decrease the free fatty acid levels in the hair follicle units
will possess more sebosuppressive effects Another aspect of the present invention is an acne biofilm. In short, the bacteria that causes acne live within the hair unit in a biofilm. No product totally rids the hair unit of *P. acnes*, and treatment is trying to alter the environment in which the bacteria live, in favor of the bacteria not producing the exocellular proteins and products that cause the inflammation of acne. It is our contention that a more potent bp (possibly as a combination of bp with a tertiary amine (or any chemical that will excite the double oxygen in bp) will significantly alter the acne biofilm. Thus, it will alter the production of *P. acnes* of extracellular proteins and substances, including hyaluronidase, proteases, lipases, and chemotatic factors for neutrophils, lymphocytes, and macrophages. In other words, it will alter the physicochemical environment of the pilosebaceous unit. It may do so not only directly via the radicals produced but by pH changes, change in oxygen tension, and alter nutrient availability. It may also likely reduce attachment of *P. acnes* to the follicular lining. Because of its superior penetration abilities, it will penetrate the extracellular matrix to reach the bacteria in the biofilm.

One of our methods of increasing the potency of bp is by favoring a base that increases benzoyl peroxide radical formation. Thus, we want to increase lability, the opposite of present treatment which try to increase stability. The benzamycin product was formulated with the knowledge that there were stability problems and the erythromycin was quickly deactivated by bp. Thus, they made the product so that with agents to slow the radical formation. We want the reaction forming bp radicals to occur as much as possible. We don't have to worry about stability of the mixture in terms of shelf life, because the patient will be mixing the two (or three or four) separate agents together himself/herself on the skin surface (most likely). We would favor a semipolar solvent with high concentration of bp (for the stronger strengths), applied at warm temperature (we may wish to heat the products up in warm water before application), we would like to have PEG 400 in the product; we would favor a very low water content of the product.

Another difference is our method of usage. In many circumstances, we would be applying two products on the skin directly, one on top of the other. (However, it is possible that there might be some indications for using bp alone with just the improvement in base.) We would suggest applying the products on the skin directly, one on top of the other. As radicals form, they can only last for a millisecond. This allows one not to miss the radicals as they form from the combination of the two chemicals. As noted in our previous work on the topic, the oxygen molecules from the bp interact especially with an available tertiary amine. Inasmuch as bp is in crystals, some radicals will form over time, but for full radical accumulation to affect the acne biofilm, one would want to catch all the radicals.

Continuing with the example of how our product would be different from the present method of using the benzamycin acne product (as an example):
We would mix them on the skin surface.
We would probably apply the antibiotic first.
We could possibly mix the two on the surface with the benefit of a transition metal. (will discuss in more detail below).
Patient mixes it up himself on the skin surface, not the palm.

In our patent we stated that transition metals also lead to more radical formation. Examples in the text included copper and iron. Thus, another method by which we might augment radical formation would be applying the bp (possibly in consort with a tertiary amine) to the skin surface, and adding one of the transition metals by means of a powder, contraption, or any other method of having contact between bp and the metal. From chemistry's periodic table, transition metals include (but are not limited to) titanium, chromium, manganese, iron, copper, nickel, cobalt, zinc silver, cadmium, and gold. Any of the transition metals (and at various positive and negative states) would be within this embodiment of this invention.

There are numerous ways in which one might use the transition metals (tm) to augment the reaction of bp. We might incorporate tm into the cream (or gel, or solution) to begin with. Then, when you mix the bp and tertiary amine, one would also be mixing it with a tm as well. Thus, it could be used as an OTC or prescription product. As a possible cosmetic, then it would fit into the definition, as any substance that is intended to be rubbed, poured, sprinkled, or sprayed on, introduced into or otherwise applied to the human body or animal body for cleansing, beautifying, promoting attractiveness or altering the appearance. This definition doesn't include soap, but our product would additionally seek that usage as well.
The tm could also be in a soap. The soap might also contain bp (with or without a tertiary amine). The soap may also contain some gritty material, such as apricot seeds, to improve the mixing on the surface. The soap may also be used in consort with an abrasive cloth or Buff-Puff.
Similarly, the tm could be used with bp (with or without a tertiary amine) as a scrubbing mixture.
(n.b. The use of tm with bp could be useful for inflammatory and comedonal (open and closed pores) acne.
the mixing of bp with tm, or bp with tertiary amines, or all three mixed together could be aided by the use of many medical devices. Such devices would include a facial steamer, message brush, ultrasound, electrical and magnetic contraptions, electrical or non-electrical toothbrush-like contraptions, combs, brushes, swabs, sandpaper/tissue paper topical measures, microdermabrasion tools, light units, heating units, the micro-electronic devices which aids delivery of ionizable compounds onto the skin, or any other method which has been previously devised for skin mixing, stimulation, or excitation. This product might be able to be used with some of the present medical devices available, or with a new medical device according to the invention. A medical device is an instrument or apparatus and parts and accessories used to diagnose, cure, mitigate, treat, or prevent disease in man or animals. Alternatively, one might use a copper, zinc, or iron comb-like agent to further augment the reaction. We might even heat the 'acne comb' slightly before use. Since the bp is in crystals, it should indeed work quite well to increase radical formation.

the tm might be mixed with bp in consort with an applicator that has a transition metal on its delivery top, or an applicator with a sponge top with metals incorporated into the sponge (or swab), or any similar contraption.

the tm might be applied in the form of any cosmetic powder, cream, lotion, or the like.

Thus, another aspect of the present invention is a new medical device (which can be defined as a medical device is an instrument or apparatus and parts and accessories use to diagnose, cure, mitigate, treat, or prevent disease in man or animals) that would aid in the mixing of a transition metal with bp (possibly in consort with a tertiary amine, for example).

We are proposing that a primary factor in the optimizing treatment with bp, is to increase its oxidizing properties. For example, one of the ways that bp exerts its antibacterial activity is by the interaction of oxidized intermediates with elements of bacterial cell walls. Thus, increasing bp radical formation will improve its effect on bacteria, fungus, biofilms, sebaceous glands, anti-skin ageing, and the like. Restated, bp exerts an oxidizing power and produces cellular effects and possible cell death via the interaction of oxidized intermediates with various constituents of microbial cells, the acne biofilm, and precancerous cells (in the case of actinic keratoses). Moreover, individuals might harbor different strains of *P. acnes* with various degrees of resistance. Thus, an agent like bp which doesn't have the normal resistance activities, would be good for such a scenario. In short, because bp exerts its antimicrobial effect through a physical interaction of oxidized intermediates which affect the bacterial cell walls, resistance to this agent is unlikely to develop.

We also propose that we may employ other methods to enhance the action of bp. Some of these methods can be classified as in the paragraph below:

Hydration which is increasing the penetration rate through the stratum corneum
- Occlusive films
- Transdermal patches Chemical enhancers (polar solvents)

Vesicles/particles
- liposomal encapsulation
- transfersomes
- ethosomes
- niosomes Physical manipulation of the stratum corneum
- photomechanical waves
- microneedles
- follicular delivery
- heat or light Electrical assisted methods
- ionophoresis
- electroporation
- sonophoresis (or phonophoresis)
- manetophoresis Expanding on one of the items above, our treatment method may include warming the face with hot water prior to application of the products. Our treatment method may be used in concert with some sun or heat lamps. Our treatment method may include heating the substances prior to application to the skin surface. There is a precedent to this, as some people use a VO5 hot oil treatment for split ends by heating the substances in hot water prior to their application.

As a short note, BP is very lipophilic and this allows it to be able to easily enter and concentrate in the lipid-rich pilosebaceous units.

Our combination could be taken in consort with either oral anti-oxidants or even topical anti-oxidants. In short, damaged cells do not respond to anti-oxidant rescue. However, normal cells respond to oxidizing agents much better when given anti-oxidant rescue. In a similar situation one may use an anticancer drug, namely methotrexate and then follows with folinic acid to rescue the cells from the low folic acid produced by the anti-cancer drug. Thus, this addition could be used in the case of using bp for actinic keratoses (pre-skin cancers) or skin cancers, where one wants to destroy the abnormal cells and preserve the normal cells. Such a method might be applicable if one uses concentrations of bp far above what is used in preparations today.

Although BP is a radical former, it may also act as an antioxidant indirectly. BP dose-dependently inhibits the release of tissue-toxic reactive oxygen species from polymorphonuclear leukocytes. This is the reason that BP is felt to have some anti-inflammatory response.

Once you put the products on the skin surface (such as benzoyl peroxide and a transition metal and/or a tertiary amine), it would be beneficial to excite the reaction by either warming the skin with heat, apply light to the skin, or by any of the items alluded to previously to energize the reaction once it is on the skin.

The benzoyl peroxice is usually at cencentrations from 0.1% to 50%. The product is normally used in between 3% and 10%, but has been used in higher concentrations for skin ulcers, for example.

An example of a product line might be:

Product A for mild acne which might contain only benzoyl peroxide in our base which makes the product more easily form radicals.

Product B for moderate acne which might contain benzoyl peroxide and a tertiary amine.

Product C for severe acne which might contain benzoyl peroxide, a tertiary amine, and a transition metal.

Product D for acne in people with outdoor work which might contain benzoyl peroxide with a transition metal such as titanium (which would also act as a sunscreen).

Our products could also be easily incorporated into a cosmetic line in all aspects of cosmetic products including soaps, creams, make-up, blush, powder, etc.

The invention would include all tertiary amines (including erythromycin) for this invention on use of the combination for fungus, hand cleansing, etc.

Following are examples of how one might incorporate transition metals with benzoyl peroxide (and possibly a tertiary amine). One might use a sunscreen which contains a transition metal (like titanium) to use on top of the bp. One then would rub them together. One also could have titanium with the benzoyl peroxide to begin with (as both are crystals in creams), and then rub them on the surface to initiate further reaction between the two molecules. Another example would be to use a metal brush, metal stone (to be similar to an emory board or pumice stone) or vibrator (such as an electric shaver without the razor, or a metal tooth-brush or an electric toothbrush). One could have an acne extractor on the other end. Another example would be using the topical agent, bp (and possibly a tertiary amine), and then using a unit such as a sonophoresis machine to use as an office device to further penetrate the product.

This use of benzoyl peroxide radicals could be used in cosmetics, detergents, toothpaste, and pharmaceuticals, etc.

In one aspect of the invention, after applying the bp and tertiary amine to the skin surface, we further augment the reaction by using some contraption which contains one of the transition metals. For example, we could use a copper, zinc or iron comb-like agent which might further augment the reaction. We might even heat the "acne comb" slightly before use. Since the bp is in crystals, it may indeed work quite well to increase radical formation.

BP is very lipophilic and this allows it to be able to easily enter and concentrate in the lipid-rich pilosebaceous units.

The invention relates to a more potent benzoyl peroxide composition. The bp may be put in a base that allows it to react more with the skin, the bacteria, and the abnormal cells in the epidermis (in the case of actinic keratoses). It is more potent because it is combined with an agent (a tertiary amine, or more liberally a nitrogen containing molecule) which makes it more powerful. By using bp with a tertiary amine, we will be producing radicals which will lead to numerous molecules being formed from the two initial molecules (the bp and the tertiary amine). The combination will lead to a quicker response and more penetration into the hair unit. Many radicals are formed quickly, and they are in a higher energy state, allowing more penetration.

Our method will be different from the present benzamycin product:

It will act as a significant pealing agent.
It will have increased comedolytic properties.
It will more significantly decrease the free fatty acid levels in the hair follicle units.
It should have more sebosuppressive effects.

Another aspect of the invention is the idea of the acne biofilm. The combination of bp with a tertiary amine will significantly alter the acne biofilm. Inasmuch, it will alter the production of *P. acnes* of extracellular proteins and substances, including hyaluronidase, proteases, lipases, and chemotatic factors for neutrophils, lymphocytes, and macrophages. In other words, it will alter the physicochemical environment of the pilosebaceous unit. It may do so not only directly via the radicals produced by by pH changes, change in oxygen tension, and alter nutrient availability. It may also likely reduce attachment of *P. acnes* to the follicular lining. Because of its superior penetration abilities, it will penetrate the extracellular matrix to reach the bacteria in the biofilm.

We are proposing that a primary factor in the optimizing treatment with bp is to increase its oxidizing properties. This is how it will have its most effect on acne, bacteria, biofilms, sebaceous glands, anti-aging of skin, and the like. BP exerts an oxidizing power and produces cellular effects and possible cell death via the interaction of oxidized intermediates with various constituents of microbial cells, the acne biofilm, and precancerous cells (in the case of actinic keratoses).

Our treatment method may include warming the face with hot water prior to application of the products.
Our treatment method may be used in concert with some sun or heat lamps.
Our treatment method may include heating the substances prior to application to the skin surface. There is a precedent to this, as some people use a VO5 hot oil treatment for split ends by heating the substances in hot water prior to their application.
Our combination would be used for all types of acne, including rosacea, adult acne, and the like.

Our combination could be taken in consort with either oral anti-oxidants or topical anti-oxidants. In short, damaged cells do not respond to anti-oxidant rescue. However, normal cells respond to oxidizing agents much better when given anti-oxidant rescue.

One aspect of the invention relates to the use of benzoyl peroxide with any tertiary amine, including erythromycin. In the past, a pharmacist mixed bp and erythromycin together to make benzamycin gel. The present invention may do several things differently:

1. We would suggest applying the products on the skin directly, one on top of the other. As radicals form, they only last for a millisecond. This allows one not to miss the radicals as they form from the combination of the two chemicals. The oxygen molecules from the bp interact especially with an available tertiary amine. Inasmuch as bp is in crystals, some radicals will form over time, but for full radical accumulation to affect the acne biofilm, one would want to catch all the radicals.
2. We would mix them on the skin surface.
3. We would probably apply the antibiotic first.
4. We could possibly mix the two on the surface with a metal contraption. Certain metals aid in radical formation.
5. Patient mixes it up himself on the surface, not the palm.
6. We would also strongly favor a base that increases lability, and decreases stability. We want the reaction to occur as much as possible right away. We don't have to worry about stability, because the patient will be mixing the two together himself/herself. We would favor a semipolar solvent with high (maybe 10% benzoyl peroxide), applied at warm temperature (we may wish to heat the products in warm water before application), we would like to have PEG 400 in the product, we would favor a very low water content of the product. The benzamycin product was formulated with the knowledge that there were stability problems and the erythromycin was quickly deactivated by bp. Thus, they made the product with agents to slow the radical formation (which coincides with erythromycin breakdown).
7. We aren't as worried about irritation, but interested in obtaining as much activity of the radicals as possible.
8. Our product may not be water-based, as water tends to decrease radical formation. Typically, it will be alcohol-based.

Additional Learnings Relating to Benzoyl Peroxide with Tertiary Amines or Trace Metals In the Treatment and/or Prevention of Various Skin Conditions In short, we have shown that benzoyl peroxide with tertiary amines (or certain trace metals) leads to catalysis with radical formation developing from both the benzoyl peroxide and the tertiary amine chemical structures. These radicals may be beneficial in numerous situations given their properties such as in antibacterial and antifungal coverage, and penetrating abilities (e.g. into hair, nails, and thicker skin). Now a mycological study (relating to fungal/yeast infections) has proved in vitro that the combination of a tertiary amine (in this case terbinafine) and benzoyl peroxide has additive benefit with most yeast organisms tested with minimum inhibitory concentrations being greatly lowered for several isolates of *Candida albicans* species.

Thus, by using the combination of a tertiary amine with benzoyl peroxide, one extends the antifungal coverage (with the obvious coverage of yeast) and antibacterial coverage. Inasmuch as these radicals probably function at the membrane level (to some extent), we are less likely to encounter resistance by microbes than with agents that operate at only the cytoplasmic and/or nuclear levels. This concept could be useful for not only prescription products, but also over-the-counter products as well.

The invention would include any tertiary amine used in association with benzoyl peroxide. In some embodiments, the invention includes any tertiary amine with the exception of erythromycin or clindamycin. Such tertiary amines include those that are over-the-counter (such as the some of the allylamines, lidocaine, pramazine, minoxidil, diphenhydramine), precription products (including many antibiotics which have tertiary amines such as other other macrolides such as clarithromycin and zithromax, and fluoroquinolones), and substances that have this chemical structure but not presently approved for any medical use at this time.

The invention extends to animal applications of the external surface (i.e. for fungal or yeast infections, bacterial infections, and the like). Similar to humans, the definition of external surfaces includes the hair, skin, nails, and oral mucosa, genital region, and nasal mucosa.

In terms of acne, our concept includes all forms of acne. This includes rosacea, perioral dermatitis, dissecting cellulitis of the scalp, pseudofolliculitis barbae, follicular keloidalis, keratosis pilaris, and all other forms that are included in major dermatological textbooks.

In terms of fungus, our concept includes all form of superficial mycological diseases including dermatophytes, candidiasis, yeast, and any other form that may be included in major dermatological textbooks. Thus, it would extend to all skin conditions that would be listed under fungal/yeast infections in a major dermatological textbook such as tinea versicolor and demodex infections. It also extends to any deep mycoses which has skin ramifications (such as skin blastomycosis). It also extends to fungal or yeast infections of the skin, nail, hair, or any other body location. Thus, onychomycosis and tinea capitis and nail candidiasis (for example) would be included under this patent. This would also include mucosal lesions such as thrush or oral candidiasis. It also extends to animal fungal/yeast infections of their fur, skin, nails, and any other exterior location.

In terms of bacteria, our concept includes all cutaneous bacterial infections of the skin that might be listed in a major dermatological textbook including such entities as folliculitis, skin ulcers (of any type) and impetigo. Our idea may also extend to pre- and/or post-surgical cleansing, insect bites, pre and/or post sexual exposure, and application to body areas such as the nasal mucosa to reduce risk of harboring 'bad' bacterial flora. Our invention would also extend to mixed bacterial and fungal infections (which often occur).

In terms of skin care, our concept includes all possible methods by one might be trying to reduce bacteria or fungal growth, regrowth, or future growth. It extends to all possible methods of daily cleansing and hygiene. This would apply to skin, hair, nail, oral, or genital areas. This would include dental care (e.g. for cleansing, for brushing, for topical application before or after brushing, for reduction of plaque, to loosen plaque and tartar, and the like), genital care (e.g. before of after sexual exposures, normal hygiene, and the like), nail care (e.g. to avoid, as well as to treat, nail infection, and normal hygiene), and for skin and hair care (e.g. for better cleansing, for better protection from the environment, and for all the other reasons that advertisers suggest that people should use and product for skin and scalp hygiene). Thus, this concept could apply to all the categories of skin, hair, and nail products that presently profess to cleanse, beautify, augment, assist, aid, correct, or affect the skin, hair, or nails in any way. These agents can be over-the-counter or prescription items. One might consider adding our concept to any or all of these health/general aids to the skin, hair, nails, oral, or genitals.

Inasmuch as our product may affect the microbial biofilms and may affect the protective lipid layers of the skin, our concept should also extend to several other disease states including viral infections (including warts and molluscum), ear wax cleansing and removal (or any other expression such as ear hygiene that may be applied), ichthyosis, psoriasis, pityriasis rosea, lichen planus, any granulomatous condition of the skin (i.e. granulom annulare and the like), age spots (i.e. seborrheic keratosis and lentigines and the like), and epidermal or sebaceous cysts (such as milia).

Inasmuch as our product may increase penetration of certain products, it may prove helpful to use in consort with various agents to assist in efficacy of the other product (or even of our product). Additionally, the radicals may affect another product when applied in consort with our product, to extend (or initiate) a desired response. Thus, one would apply benzoyl peroxide with a tertiary amine to the skin (hair, nails, or mucosa) with an additional substance (either before or after, either in consort or at a different time, either preformed or separate) so as to potentiate (or initiate) some desired result. This concept could be useful in a vast array of dermatological states, in fact, it could be useful in any state listed in any dermatological textbook (such as alopecia areata, scars, pigmentary alterations, and the like) or any condition that is addressed by beauticians or any condition that has a product sold at the larger drug stores under cosmetics, cleansers, soaps, shampoos, gels, liquids, lotions, creams, pastes, ointments, covering agents, mascara, shaving products, bath products, and everything else that is presently sold (or will be sold under some other name in the future). The invention can also be used for beautifying skin such as anti-wrinkling and/or cosmesis.

In terms of antifungal/antiyeast therapy, this invention also extends to using benzoyl peroxide by itself (without an additive product) for the treatment of topical fungal/yeast infections (as defined above).

Also, this invention extends the use of benzoyl peroxide with other agents that are presently used in the treatment of fungal disease. Thus, besides allylamines, one could use BP in consort with (either simultaneously, before, after, in one or two containers) with any of these agents: Whitfield's ointment, Castellani's paint, undecylenic acid, tolnaftate, imidazole compounds (such as miconazole, cholrtrimazole, oxiconazole, econazole, ketoconazole, etc.), cycloprox olamine, naftifine, oxiconazole and sulconazole, lotrasone, polyenes (such as amphotericin B and nystatin), griseofulvin, haloprogin, or any other agent or chemical that might be advantageous to use in consort with benzoyl peroxide for treatment of fungal/yeast infection. Also, inasmuch as mixed infections of fungus and bacteria sometimes occurs, this provisional patent would extend to include the entire above list above of antifungals to be used in consort with benzoyl peroxide for these mixed infections as well (the use of BP with allylamines for mixed infections was covered in an earlier paragraph).

Use of Benzoyl Peroxide with Allylamines

Benzoyl peroxide (BP) topically acts antibacterially, keratolytically, has anti-lipolytic activity, and reduces bacteria in the follicular infundibula. BP has bacteriocidal and bacteriostatic properties to many cutaneous microorganisms in vitro including *Propionibacterium acnes, Staphylococcus capitis, Staphylococcus epidermidis, S. hominis, P. Avidum, P. granulosum*, and *Pityrosporum ovale*. Indeed, significant reduction in propionibacteria and Micrococcaceae were noted after 2 days of usage of topical BP. The suppression was more rapid and to a greater degree than that achieved with topical antibiotics alone. BP has increased antibacterial property against several species of *P. acnes* when incubated in vitro in the presence of a lipid mixture. The significance may not only reflect the chemical's good lipid solubility but suggests that in a biofilm situation, as applies within the sebaceous follicle, BP may advantageously penetrate this protective bacterial shielding.

Tertiary amines are the most commonly used activators of the BP initiator for curing composite restorative resins and acrylic bone cements. BP is also one of the most commonly applied initiators, reacting through a one electron transfer with lower oxidation state metals to initiate polymerization. Thus, the tertiary amine is the active ingredient which induces reaction of the BP giving rise to free radicals capable of initiating polymerization in the curing of the acrylic monomers for bone cements.

Clinically, the combination of BP with erythromycin (a tertiary amine) has shown excellent clinical results. The combination of topical erythromycin or clindamycin with benzoyl peroxide is more effective that either the antibiotic or benzoyl peroxide alone for the treatment of acne. This combination greatly outperforms tretinoin with erythromycin in clinical acne, with clinical differences appearing within 2 weeks of usage.

In terms of acne, BP with one tertiary amine, namely erythromycin, has been studied. Five erythromycin resistant strains (out of 40) were inhibited in vitro synergistically or additively, by the combination. Given the concept of the *P. acnes* biofilm, this antibacterial profile may be sufficient to alter the biofilm so that the enzymes and toxins produced within the biofilm are sufficiently altered to obtain a good clinical result. Clinical in vivo bacterial studies have also shown a reduction of micrococcaceae in the pilosebaceous ducts. Also BP with erythromycin lead to significant reduction (3 log reduction) in *P. acnes* organisms after 6 weeks of topical use, including organisms otherwise resistant to erythromycin.

The exact site of BP activity, whether used alone or in consort with a tertiary amine, is not well appreciated. Its major action would be on bacterial cell walls and the *P. acnes* biofilm, but whether the activity is on the mucopolysaccharide matrix of the biofim of some of the bacterial components of the biofilm is poorly appreciated. Inasmuch as biofilms function as a unit, it could be assumed that any disruption of the biofilm could be advantageous in the diseased state. BP also produces free radicals which that can induce damage to bacterial DNA and its components.

Addressing one aspect of this possible interaction, one could consider that these BP radicals better attack the cell walls. Fungus and bacteria are encased in a cell wall, while mammalian cells are not. Therefore, inhibition or destruction of cell walls is a useful mode of action for antifungal and antibacterial agents. Bacteria form the cell wall via peptidoglycan biosynthesis. This biological polymer is unique to bacteria and contains both L- and D-isomers of its constituent amino acids. Antibiotics may act at several stages during peptidoglycan synthesis, cross-linking of peptidoglycans, or cause actual damage to the bacterial cell wall. It can be postulated that the formation of BP radicals and radicals formed from the tertiary amine, may act by altering the bacterial cell walls of the sensitive organism within the *P. acnes* biofilm. It can be postulated that drugs that function at the membrane level are less likely to encounter resistance by antimicrobial agents than drugs that operate at the cytoplasmic and nuclear levels.E This begins to explain the finding that the addition to erythromycin to BP eliminates some otherwise resistant organisms.

In terms of antifungal activity, derivatives of tertiary amines (like terbinafine) which are less bulky (which can occur with radical formation) often have stronger potency in terms of combating skin fungal,S or nail fungus. Molecular size of the penetrating drug (or radical) is of paramount importance. Substitution of the basic structure of terbinafine, as occurs with radical formations, significantly enhance the activity of this drug against *Candida albicans*.

In regards to oxidation of amines, this chemical reaction can be affected by temperature.

Testing of Terbinafine in Combination with Benzoyl Peroxide Against *Candida Albicans*

Objective

The object of this preliminary study was to discover the in vitro effect of the addition of benzoyl peroxide to terbinafine when tested against *Candida albicans, Pseudomonas aeruginosa*, and *Staphylococcus aureus* isolates, using a checkerboard microdilution method.

Procedure

The checkerboard combination test method is a modification of the microdilution antifingal susceptibility test (NCCLS M27A) wherein two antifingal agents are combined in varying concentrations to determine whether they have a synergistic, additive, or antagonistic effect on the respective minimum inhibitory concentration (MIC) values.

Two antifungal agents are serially diluted in a desired medium to produce ten concentrations of the drugs under investigation. The range is chosen to include achievable serum levels of the drugs. The two drugs are then combined into wells of a microtiter plate so that the concentration of one drug increases as that of the other decreases. Two rows consisting of serial dilutions of each individual drug are also included. Comparison of the MICs of the individual antifungal agents to the MIC of the combined agents is indicative of their relative efficacy.

In this proposed study, ten serial dilutions of terbinafine (beginning at 32 µg/ml) and benzoyl peroxide (beginning at 3%) were tested alone and in combination against ten *Candida albicans* isolates taken from the culture collection at the Center for Medical Mycology. Both susceptible and fluconazole-resistant strains were included. In addition, two strains of *Pseudomonas aeruginosa* and two strains of *Staphylococcus aureus* were also tested.

Data Analysis

The MIC for both terbinafine and benzoyl peroxide was defined as the lowest concentration to inhibit 80% of visual growth as compared to the growth control (no drug exposure).

Combination susceptibility studies by the checkerboard method are reported as the Factional Inhibitory Concentration Index($FICI$) =

$$\frac{MIC \text{ drug } A \text{ in combination}}{MIC \text{ drug } A \text{ alone}} + \frac{MIC \text{ drug } B \text{ in combination}}{MIC \text{ drug } B \text{ alone}}$$

The combination of two drugs is reported as:
Synergistic=<0.5
Additive=0.5<FICI <1.0
Indifferent=1.0<FICI <4.0
Antagonistic=>4.0

FICI determinations were made from the results of visual endpoints.

Results

MICs of Individual Compounds

| Organism | Terbinafine | | | Benzoyl Peroxide | | | | | |
|---|---|---|---|---|---|---|---|---|---|
| | >32 μg/ml | 16 μg/ml | 8 μg/ml | 3.0% | 1.5% | 0.75% | 0.38% | 0.19% | 0.09% |
| C. albicans (n = 10) | 9 | | 1 | 4 | | | 6 | | |
| Ps. aeruginosa (n = 2) | 2 | | | | | | | | 2 |
| S. aureus (n = 2) | 2 | | | | 2 | | | | |

MICs (in μg/ml) of Terbinafine in Combination with Benzoyl Peroxide

| Organism | >32 | 16 | 8 | 4 | 2 | 1 | .5 | .25 | .125 | .06 | .03 | <.03 |
|---|---|---|---|---|---|---|---|---|---|---|---|---|
| C. albicans (n = 10) | 1 | 6 | 1 | 1 | 1 | | | | | | | |
| Ps. aeruginosa (n = 2) | | | | | | | | | 1 | | 1 | |
| S. aureus (n = 2) | | | | | | | | | | | 2 | |

MICs (%) of Benzoyl Peroxide in Combination with Terbinafine

| Organism | 3 | 1.5 | .75 | .38 | .19 | .09 | .05 | .02 | .01 | .006 | .003 |
|---|---|---|---|---|---|---|---|---|---|---|---|
| C. albicans (n = 10) | 1 | 3 | | 6 | | | | | | | |
| Ps. aeruginosa (n = 2) | | | | | 2 | | | | | | |
| S. aureus (n = 2) | | | 2 | | | | | | | | |

FICI Interpretations

| Organism | Synergistic | Additive | Indifferent | Antagonistic |
|---|---|---|---|---|
| C. albicans (n = 10) | | 8 | 2 | |
| Ps. aeruginosa (n = 2) | | | 2 | |
| S. aureus (n = 2) | | | 2 | |

Discussion

As expected, all of the *C. albicans* isolates were resistant to terbinafine, with MICs >32 μg/ml. Combinations of terbinafine and benzoyl peroxide were additive against eight (80%) *C. albicans* isolates and indifferent against the remaining two *C. albicans* isolates. Interestingly, the MICs of terbinafine in combination were lowered significantly for two *C. albicans* isolates.

All of the bacterial isolates were also resistant to terbinafine alone, with MICs >32 μg/ml. Though the combination of terbinafine and benzoyl peroxide did not lower the MIC of benzoyl peroxide, accounting for the indifferent FICI interpretations, the MIC of terbinafine in combination against all bacterial isolates was lowered significantly.

Importantly, there was no antagonism noted with the combination of terbinafine and benzoyl peroxide against any isolate. The in vivo significance of this data remains to be established.

Additional Uses in Skin Products for Benzoyl Peroxide with Tertiary Amines or Trace Metals The invention may be beneficial in numerous skin products including soaps, shampoos, bath products, shaving products, antibacterial and antifungal topical agents, dentrifices, hair bleaches and boosters, nail products, bleaching creams, nail polish, mascara, skin dressings, cosmetics and covering agents, gels, liquids, powders, lotions, creams, pastes, gels, and ointments. Again, the addition could be a tertiary amine or a trace metal. For example, the use of benzoyl peroxide with a tertiary amine (like thos found in terbenefine, miconazole, tolnaftate, ketoconazole) should prove to have more antibacterial and antifungal properties that would have benefit in soaps, shampoos, creams, and the like. It also would have benefit for bacterial and fungal infections of the skin, hair and nails. It would also be an excellent choice in proper formulation to favorably compete with penlac in efficacy for nail fungus. The use of benzoyl peroxide with a different tertiary amine (like diphenhydramine) may be a better topical antihistamine for use of patient symptoms of itch or welting. The use of benzoyl peroxide with a tertiary amine (like minoxidil) may have better efficacy. The use of benzoyl peroxide with a tertiary amine (like lidocaine or pramazine) would be beneficial for patients with pruritus, eczema, or similar complaints. Such a product may also be very beneficial for patients with itching in specific areas of the body such as the armpits, ears, scrotum, scalp, and skin.

Several of these agents could be used in consort. For example, for underarm itch, one could use an anesthetic, an antifungal and benzoyl peroxide. In this particular instance of itching of the armpits and other skin areas (such as the scrotum, ears, and scalp), we extend this invention to include the use of an antipruritic agent along with an antiperspirant or deodorant, even without the use of benzoyl peroxide.

Use of the Compositions for Skin Aging

The compositions of the invention containing benzoyl peroxide and a tertiary amine, and/or a transition metal, may be used to prevent skin aging. The concept is that liver spots (in particular) may be preventable (to a great extent) with the use of this combination therapy. The melanosomes that are produced in this disease would seemingly be a response to some lipopolysaccharide or peptidoglycan from an altered microbe on the skin surface, or in the skin stratum corneum. This idea is from how melanin, melanosomes, and melanocytes work in invertebrates (and in man to some extent). The use of the combination should reduce these microbes and avoid the response to the alteration in the messages sent to the melanocytes.

Tertiary Amines and Benzoyl Peroxide Radicals: Testing of Terbinafine in Combination with Benzoyl Peroxide Against *Candida Albicans, Pseudomonas Aeruginosa*, and *Staphylococcus Aureus*

Abstract

Dermatophyte infections can be polymicrobial. Topical antifungal therapies offer limited coverage of yeast and gram-positive and gram-negative bacteria. Moreover, the increased usage of these topical antimicrobial agents has resulted in the development of resistant cases to these therapeutic agents. Benzoyl peroxide used in consort with antimicrobial agents, which contain an accessible tertiary amine, has previously been shown to increase radical activity and biological effect. In this study, the combination of benzoyl peroxide with terbinafine lead to additive activities against the majority of *Candida albicans* isolates tested and additionally expanded the bacterial coverage of terbinafine. Further appreciation of this mechanism of catalysis of benzoyl peroxide radical formation by certain antimicrobials and other tertiary amine containing compounds may lead to the discovery of improved treatments for several dermatologic states.

Background: Topical antifungal therapies offer limited coverage of yeast and gram-positive and gram-negative bacteria. Moreover, the increased usage of these topical antimicrobial agents has resulted in the development of resistant cases to these therapeutic agents. Benzoyl peroxide used in consort with antimicrobial agents, which contain an accessible tertiary amine, has previously been shown to increase radical activity.

Objective: The aim of this study was to assess whether benzoyl peroxide used in consort with antimicrobial agents, which contain an accessible tertiary amine, increases biological effect against bacteria and fungus.

Methods: In this preliminary in vitro study, the effect of BP, alone and in combination with terbinafine, was tested against *C. albicans, Pseudomonas aeruginosa*, and *Staphylococcus aureus* isolates, following a checkerboard modification of the National Committee for Clinical Laboratory Standards.

Results: In this study, the combination of benzoyl peroxide with terbinafine lead to additive activities against the majority of *Candida albicans* isolates tested and additionally expanded the bacterial coverage of terbinafine.

Conclusion: Our data suggests that benzoyl peroxide when used in consort with an antifungal containing a tertiary amine, like terbinafine, catalyzes formation of radicals, produces a biological synergism, is a promising antifungal agent for both yeast, filamentous fungi, and bacteria, and warrants further testing in vivo.

Dermatophyte infections are one of the world's most common skin diseases. Superficial fungal infections invade keratinous tissue of the skin, hair, and nails. Yeast and bacteria often accompany dermatophytes as co-contributors to the pathogenesis of skin infections. The main therapeutic agents employed in the topical treatment of these infections are the polyenes, imidazoles, allylamine, and ciclopirox olamine drugs. The first three of these classes of antifungals act by altering ergosterol, an essential component of fungal cell membranes. The mode of action of ciclopirox olamine is less specific, and is believed to target a variety of metabolic processes in the fungal cell.

Improvement in topical antifungal therapy would be welcomed given the limited coverage of yeast and gram-positive and gram-negative bacteria by many of these topical remedies. Moreover, the increased usage of these topical antimicrobial agents has resulted in the development of resistant cases to these therapeutic agents. Thus, adjunctive agents which may have synergistic, or additive, activity against dermatophytes, as well as these mixed infections, would be greatly appreciated in dermatologic therapy.

Benzoyl peroxide (BP), used in consort with certain antifingal agents, may demonstrate broader antimicrobial activity against bacteria and yeast than either agent used alone. This hypothesis is based on our previous work which demonstrated that the radical activity of BP is increased when tested in consort with chemical structures which contain a tertiary amine within its structure. In acne, the concomitant topical treatment of BP with certain antibiotics that possess an accessible saturated nitrogen molecule, such as erythromycin, appears to be more effective clinically than the use of either of these agents alone. Increased radical activity and enhanced biological effect by means of this mechanism suggests the possibility of biological synergism in antimicrobial therapy.

Terbinafine has previously been shown to be highly active against dermatophytes and several other filamentous fungi. This drug is also considerably effective against a broad range of yeast in vitro. More pertinent to this study, terbinafine has a chemical structure which has an accessible tertiary amine for possible interaction with BP. In short, this study assesses whether the addition of BP to terbinafine augments the spectrum of antiyeast and antibacterial coverage of terbinafine.

The combination of BP with tertiary amines has not been previously studied for antifungal activity. In this preliminary in vitro study, the effect of BP, alone and in combination with terbinafine, was tested against *C. albicans, Pseudomonas aeruginosa*, and *Staphylococcus aureus* isolates, following a checkerboard modification of the National Committee for Clinical Laboratory Standards M38A and M27A2.

Materials and Methods:

Organisms:

In this study, ten serial dilutions of terbinafine (starting at 32 µg/ml) and benzoyl peroxide (starting at 3%) were tested alone and in combination against ten *Candida albicans* isolates from the culture collection at the Center for Medical Mycology. Both susceptible and fluconazole-resistant strains were included. Two strains each of *Pseudomonas aeruginosa* and *Staphylococcus aureus* were also tested.

MIC Determinations:

The individual minimum inhibitory concentrations (MICs) of terbinafine and BP against each isolate were determined according to the NCCLS M27-A2 and M07-A6 standards for yeasts and aerobic bacteria, respectively. The MIC endpoints were defined as the lowest concentration that inhibited 80% of growth as compared to the growth control.

In Vitro Combination Analysis:

The effect of combining benzoyl peroxide with terbinafine was evaluated using a checkerboard assay. This test method is a modification of the microdilution antifungal susceptibility test (NCCLS M27A2) wherein two antifungal agents are combined in varying concentrations to determine whether they have a synergistic, additive, or antagonistic effect on the respective minimum inhibitory concentration (MIC) values.

Two antifungal agents were serially diluted in RPMI to produce ten concentrations of the drugs under investigation. The range was chosen to include achievable serum levels of the drugs. The two drugs were then combined into wells of a microtiter plate so that the concentration of one drug increases as that of the other decreased. Two rows consisting of serial dilutions of each individual drug were also included. Comparison of the MICs of the individual antifungal agents to the MIC of the combined agents was indicative of their relative efficacy.

Data Analysis

The MIC for both terbinafine and benzoyl peroxide was defined as the lowest concentration to inhibit 80% of visual growth as compared to the growth control(no drug exposure). FICI determinations were made from visual endpoints. Combination susceptibility studies by the checkerboard method were reported as the Fractional Inhibitory Concentration Index(FICI) =

$$\frac{MIC \text{ drug } A \text{ in combination}}{MIC \text{ drug } A \text{ alone}} + \frac{MIC \text{ drug } B \text{ in combination}}{MIC \text{ drug } B \text{ alone}}$$

The combination of two drugs was reported as synergistic (<0.5), additive (0.5<FICI <1.0), indifferent (1.0<FICI <4.0), or antagonistic (.4.0).

Results

The individual MICs of terbinafine and BP are shown in the following table:

| Organism | Terbinafine | | | Benzoyl Peroxide | | | | | |
|---|---|---|---|---|---|---|---|---|---|
| | >32 µg/ml | 16 µg/ml | 8 µg/ml | 3.0% | 1.5% | 0.75% | 0.38% | 0.19% | 0.09% |
| *C. albicans* (n = 10) | 9 | | 1 | 4 | | | 6 | | |
| *Ps. aeruginosa* (n = 2) | 2 | | | | | | | | 2 |
| *S. aureus* (n = 2) | 2 | | | | 2 | | | | |

The following table shows the MICs (in µg/ml) of terbinafine in combination with BP for each isolate.

| Organism | >32 | 16 | 8 | 4 | 2 | 1 | .5 | .25 | .125 | .06 | .03 | <.03 |
|---|---|---|---|---|---|---|---|---|---|---|---|---|
| *C. albicans* (n = 10) | 1 | 6 | 1 | 1 | 1 | | | | | | | |
| *Ps. aeruginosa* (n = 2) | | | | | | | | | 1 | | | 1 |
| *S. aureus* (n = 2) | | | | | | | | | | | | 2 |

The following table shows the MICs (%) of B— P— in combination with terbinafine for each isolate.

| Organism | 3 | 1.5 | .75 | .38 | .19 | .09 | .05 | .02 | .01 | .006 | .003 |
|---|---|---|---|---|---|---|---|---|---|---|---|
| *C. albicans* (n = 10) | 1 | 3 | | 6 | | | | | | | |
| *Ps. aeruginosa* (n = 2) | | | | | | | 2 | | | | |
| *S. aureus* (n = 2) | | | 2 | | | | | | | | |

As expected, all of the *C. albicans* isolates were resistant to terbinafine, with MICs >32 μg/ml. Combinations of terbinafine and benzoyl peroxide were additive against eight (80%) *C. albicans* isolates and indifferent against the remaining two *C. albicans* isolates. Interestingly, the MICs of terbinafine in combination were lowered significantly for two *C. albicans* isolates.

All of the bacterial isolates were also resistant to terbinafine alone, with MICs >32 μg/ml. Though the combination of terbinafine and benzoyl peroxide did not lower the MIC of benzoyl peroxide, accounting for the indifferent FICI interpretations, the MIC of terbinafine in combination against all bacterial isolates was lowered significantly.

Importantly, there was no antagonism noted with the combination of terbinafine and benzoyl peroxide against any isolate. The in vivo significance of this data remains to be established.

Discussion

Our studies reveal that combining BP with terbinafine led to additive activity against the majority of *C. albicans* isolates, with no antagonism noted for either fungal or bacterial isolates. Additionally, the minimum inhibitory concentration of terbinafine in combination with BP was lowered significantly against all bacterial isolates. This supports our previous in vitro study demonstrating that the catalysis of BP radical activity can be augmented by the concomitant therapy of BP with an antimicrobial agent which contains a tertiary amine within its structure.[2] Assuming that increased radical formation correlates with enhanced biological effect, this in vitro study suggests a biological synergism in mixtures of BP with chemicals which structurally offer an accessible tertiary amine. These radicals would form both from the BP molecule as well as from the corresponding N-oxide and complex product mixtures via radical decomposition of the chemical initially containing the tertiary amine.

Certainly most of the studies with BP in dermatology have focused on its use in acne. BP topically acts antibacterially, keratolytically, has anti-lipolytic activity, and reduces bacteria in the follicular infundibula. BP has shown to have bactericidal and bacteristatic properties against many cutaneous microorganisms in vitro, including *Propionibacterium acnes, Staphylococcus capitis, Staphylococcus epidermidis, S. hominis, P. Avidum, P. granulosum,* and *Pityrosporum ovale*. Indeed, significant reduction in propionibacteria and micrococcaceae were noted after 2 days of usage of topical BP. The suppression was more rapid and to a greater degree than that achieved with topical antibiotics alone.

Chemically, tertiary amines are the most commonly used activators of the BP initiator for curing composite restorative resins and acrylic bone cements. BP is also one of the most commonly applied initiators, reacting through a one electron transfer with lower oxidation state metals to initiate polymerization. Thus, tertiary amines initiate chemical reactions with BP resulting in the formation of free radicals capable of initiating polymerization in the curing of the acrylic monomers for bone cements.

In dermatology, the combination of BP with a tertiary amine has only been applied in the area of acne. In this case, the tertiary amine, as chemically present in the drug erythromycin, has been used in consort with BP, with excellent clinical results. Indeed, clinical trial results have shown that the combination of topical erythromycin with BP is more effective than either the antibiotic or BP alone for the treatment of acne. The joint treatment of BP and this tertiary amine also greatly outperforms tretinoin with erythromycin in clinical acne, with clinical differences appearing within 2 weeks of usage.

Indeed, five erythromycin-resistant strains (out of 40) were inhibited in vitro synergistically or additively, by the combination. Clinical in vivo bacterial studies have also shown superior reduction of micrococcaceae in the pilosebaceous ducts with this concurrent therapy. Additionally, BP with erythromycin lead to significant reduction (3 log reduction) in *P. acnes* organisms after 6 weeks of topical use, including organisms otherwise resistant to erythromycin.

The exact site of BP activity, whether used alone or in consort with a tertiary amine, is not well characterized. Its major action may be on antimicrobial cell walls and/or the acne or fungal biofilm, BP also produces free radicals within cells that can induce damage to microbial genetic material, as well as a variety of metabolic processes in the fungal cell.

In regards to antifungal activity, the combination of BP with tertiary amines has not been previously studied. However, derivatives of tertiary amines formed from the radical decomposition of the terbinafine molecule would be less bulky, which can signify stronger potency in terms of combating skin or nail fungus. Molecular size of the penetrating drug, or radical thereof, is of paramount importance. Previously, substitution of the basic structure of terbinafine, as occurs with radical formations, have been shown to significantly enhance the activity of this drug against *C. albicans*.

The results of this study may suggest that the combination of an antifungal bearing a tertiary amine with benzoyl peroxide would be beneficial, given its wider spectrum of antimicrobial coverage. Indeed, there is reason to believe that in vivo studies may surpass in vitro results given a necessary defect in the laboratory study. In this in vitro assessment, terbinafine and BP were serially diluted separately and then combined in empty wells. The inoculum was then added to all the wells. The dissolving process of BP involved microwaving the powder in DMSO for 8 to 10 seconds. Thus, there was a significant delay before the isolates were exposed to the combination of a tertiary amine with BP. Although the radicals may not form instantly, once formed, they exist for less than a second. Future studies must better account for this delay in processing the mixed therapeutic agent. Additionally, the radicals formed by this combination therapy may well prove to penetrate better than present treatment modalities, which may prove beneficial in thick-skinned areas, such as the soles of feet, as well as in fungal treatment of nails and where fungal biofilms are present.

In conclusion, our data suggests that BP when used in consort with an antifungal containing a tertiary amine, like terbinafine, catalyzes formation of BP radicals, and is a promising antifungal agent for both yeast, filamentous fungi, and bacteria, and warrants further testing in vivo. These findings may have implication in the use of these antimycotics in the treatment of mixed cutaneous infections in which bacteria or yeast are present in addition to dermatophytes. Such a combination therapy may also better control the emergence of antifungal resistance by these dermatophyte species. An agent with the broadest in vitro activity against bacteria, yeasts, and bacteria may be preferred in treatment of most dermatophyte infections. Further appreciation of this mechanism of catalysis of BP radical formation by certain antimicrobials and other compounds, may lead to the discovery of improved treatments for several dermatological states.

Enhanced Acne Therapy with Tertiary Amines and Benzoyl Peroxide Radicals: Comparison Testing of Butenifine in Combination with Benzoyl Peroxide vs. Proactiv Solution Abstract:

Background: Concerns have arisen over the development of antibiotic-resistant organisms due to the prolonged use of oral and topical antibiotics in acne vulgaris. Many have suggested limiting the use of topical and systemic antibiotics to only severe cases, and to avoid their use in maintenance therapy. On this point, we have previously demonstrated that benzoyl peroxide used in consort with a chemical with an accessible tertiary amine, such as an allylamine, increases radical activity and possibly biological effect.

Objectives: The purpose of this pilot study is to assess patient satisfaction with two non-antibiotic topical remedies for mild to moderate acne, with one of the agents being a combination of benzoyl peroxide with butenifine, an allylamine.

Methods: In an open-label, 8-week, comparative study, 23 patients demonstrating mild to moderate facial acne were given randomly either benzoyl peroxide in the form of the highly marketed, over-the-counter, Proactiv Solution, or the combination of benzoyl peroxide with an allylamine. Study subjects self-counted comedones and inflammatory acne lesions as well as degree of oiliness at the onset, and every two weeks during the study. Additionally, the subjects were asked complete a 10-question survey to assess their satisfaction with the tested products.

Results: The allylamine/benzoyl peroxide combination therapy outperformed Proactiv Solution during each two-week stage of evaluation in terms of reduction of comedones, inflammatory lesions, and degree of oiliness. There was a marked preference for the allylamine/benzoyl peroxide combination in terms of patient satisfaction.

Conclusions: Benzoyl peroxide used in consort with antimicrobial agents which contain an accessible tertiary amine, such as erythromycin, has previously been shown to increase radical activity and biological effect. In vitro studies have revealed that catalysis of benzoyl peroxide radical formation can also be achieved with allylamines. Trials of short duration with small numbers of patients do not adequately inform practitioners whether the combination of allylamines with benzoyl peroxide is a viable alternative to topical antibiotic therapy for acne. However, the higher satisfaction with the allylamine/benzoyl peroxide combination certainly warrants further investigation.

Acne is the most common skin disease of man, affecting the vast majority of adolescents and young adults. Dogma states four contributing factors to acne including sebum production, abnormal keratinization with the pilosebaceous unit, proliferation of *Propionibacterium acnes* within the pilosebaceous unit, and perifollicular inflammation. Recent evidence suggests that the *P. acnes* biofilm may play the central role in acne pathogenesis.

Drug regimens that affect these etiological factors have been shown to improve acne. In particular, antibiotic-based treatment regimens are considered by many to be the first-line in topical and systemic therapies for acne. With the recent association of use of antibiotics with increased risk of breast cancer, the American Academy of Dermatology has again encouraged its members to carefully select patients for chronic antibiotic therapy and limit the long-term use of antibiotics for acne.

Previously, concerns have been expressed over the development of antibiotic-resistant organisms in the acne pilosebaceous units, by use of both oral and topical antibiotics. A negative relationship has been seen between the carriage of resistant strains to clindamycin, tetracyclines, erythromycin, and trimethoprim-sulfamethoxazole in *P. acnes* and the reponse to acne therapy with the corresponding antibiotic. Reports of incidence of antibiotic resistance of *P. acnes* has gradually increased form 35% in 1991 to as high as 94% in 2003. Moreover, this resistance may limit antibiotic effectiveness for other dermatological conditions and non-dermatological infectious disease states.

Some authors have suggested that avoidance of topical (including the popular combination agents such as erythromycin/benzoyl peroxide, clindamycin/benzoyl peroxide, erythromycin/isotretinoin, erythromycin/tretinoin) and systemic antibacterial therapy for acne as much as possible. When necessary, it has been suggested to keep antibiotic courses short and avoid using oral or topical antibiotics for maintenance therapy.

There are several alternatives to antibiotics for the management of inflammatory acne. Most notably, benzoyl peroxide is a non-antibiotic, antibacterial agent that is bactericidal against *P. acnes*. Indeed, a major aspect of this study is to determine if clinically one could improve the efficacy of benzoyl peroxide for acne by means of a combination product besides an antibiotic. In this study, an allylamine was used as a possible amplifier of benzoyl peroxide radical activity. The topical preparation that was used in our study as the traditional, standard, benzoyl peroxide was Proactiv Solution made by Guthy-Renker, which is by far the largest selling acne product in America with stated profits of over 300 million per year. This over-the-counter product uses a three-step-system in which benzoyl peroxide is the only active ingredient in both the cleanser and the repairing lotion.

We have previously shown that the radical activity of benzoyl peroxide is increased when tested in consort with chemical structures which contain a tertiary amine within its structure. Additionally, we have demonstrated that benzoyl peroxide used in combination with the allylamine antifungal agents, has broader antimicrobial activity against bacteria and yeast than the either agent used by itself. This complies with the belief that benzoyl peroxide may exert its antibacterial activity by the interaction of oxidized radical intermediates with elements of the bacterial cells. In acne, the concomitant topical treatment of BP with certain antibiotics that possess an accessible saturated nitrogen molecule, such as erythromycin, is more effective clinically than the use of either of these agents alone. Increased radical activity and enhanced biological effect by means of this mechanism, suggests the possibility of biological synergism in antimicrobial therapy.

Butenifine is one of the allylamine antifungal agents, and has a chemical structure which has an accessible tertiary amine for interaction with BP forming radicals. In short, this study assesses whether the radicals formed by the addition of an allylamine to benzoyl peroxide augments the therapeutic effect of benzoyl peroxide in acne.

Study Design:

This study was an open-label comparison designed to examine patient satisfaction with benzoyl peroxide versus a combination of benzoyl peroxide and butenifine for facial acne. Twenty-six patients, ranging in age from 15 to 35 and demonstrating mild to moderate acne were recruited from patients from a dermatology office as well as from solicitations to two area high schools from September, 2003 to March, 2004. All patients had a Leeds revised acne grading system score of 2.0 to 7.0 and a count of at least 10 but no more than 50 of both inflamed and non-inflamed lesions on the face. Study subjects were excluded if they had acne conglobata, acne fulminans, secondary acne, or cystic acne. Also pregnant, breast-feeding, or patients with underlying diseases or other dermatological conditions were excluded. Study subjects also could not have been on any prescription acne therapy within the prior 3 months.

Study subjects using the three-step Proactiv Solution approach were given three containers which were devoid of the commercial name of the product. Following the usage guidelines of the product, patients were instructed to apply solution #1 (designated as the renewing cleanser in the Proactiv Solution format) to the face before rinsing off with water. Then the patient was instructed to apply solution #2 (the revitalizing toner) to the face, followed after one minute by the application of solution #3 (repairing lotion) on top of solution #2.

Patients using the benzoyl peroxide with the allylamine were instructed to twice daily cleanse their face with cetaphil washing lotion. They were then instructed to apply the allylamine to the face followed within seconds by the application of benzoyl peroxide cream. The patients were instructed to mix the two products on the facial skin surface.

Patients were seen at a screening visit and at the completion of the study. Return visits were encouraged if patients experienced any side effects, or if they desired physician observation. All patient visits were conducted in the private office setting. Patients were screened by evaluating the grade of acne and the number of lesions. Patients were randomized into two equal groups corresponding to the chronological order of study entry to receive either benzoyl peroxide in the form of the Proactiv Solution or the combination of benzoyl peroxide and butenifine. Patients were given diary charts to complete to record his/her determination of number of inflamed and non-inflamed lesions and degree of facial dryness every two weeks during the study. After 8 weeks of treatment, patients completed a self-assessment questionnaire about their assessment of treatment. Utilizing a 10-point scale (1 meaning 'definitely didn't help,' to 10 meaning 'did a fantastic job') patients were asked to rate their responses to several clinical parameters.

Results:

Of the 26 patients recruited, 23 completed the study, 12 from the Proactiv group, and 11 from the benzoyl peroxide/allylamine section. Inasmuch as every patient had a different baseline in terms of acne counts and oiliness, the efficacy variables were tabulated in terms percentage degree of improvement for both treatment modalities (FIGS. 1 and 2). In this study, the allylamine/benzoyl peroxide therapy outperformed ProActiv Solution during each two-week stage of evaluation and by all three parameters evaluated. The allylamine/benzoyl peroxide therapy reduced the number of open and closed comedones by 64% and degree of facial oiliness by 51% by eight weeks, in comparison to figures of 16% and 36% for Proactiv Solution. The difference in the percentage of improvement in the number of facial inflammatory lesions was less marked, with 39% reduction with allylamine/benzoyl peroxide and 34% with Proactiv Solution.

The patients' ratings of the two topical preparations on several clinical parameters were tabulated, and the averages are shown in Table 3. Although both agents improved the acne condition, the benzoyl peroxide/allylamine combination outperformed Proactiv Solution on all questioned posed. Of note, there was a 3-point differential in patient satisfaction with the overall treatment results between the two products. There was also more than a 2-point differential in treatment performance favoring benzoyl peroxide/allylamine in reducing the severity of acne and the number of acne lesions, preventing breakouts, and improvement in feeling comfortable and confident. Thus, although the number of inflammatory lesions was only slightly better with benzoyl peroxide/allylamine combination, the degree of inflammation of those lesions was significantly less with this therapy. There were minimal differences in the patient assessment of facial softness and smoothness between the two products. These latter two parameters are suggested to be benefited by the use of Proactiv Solution in their advertisements.

Discussion:

This pilot study suggests that combining benzoyl peroxide with butenifine leads to additive clinical benefits for mild and moderate acne. More specifically, the addition of an allylamine to benzoyl peroxide further reduced the amount of comedonal and inflammatory acne as well as decreased skin oiliness. This supports our previous in vitro study demonstrating that the catalysis of benzoyl peroxide radical activity can be augmented by the concomitant therapy of benzoyl peroxide with a substance which contains an accessible tertiary amine within its structure. Assuming that increased radical formation correlates with enhanced biological effect in acne, this patient satisfaction study suggests a biological synergism exists in mixtures of benzoyl peroxide with allylamines. On passing these radicals would form both from the benzoyl peroxide molecule as well as form the corresponding N-oxide and complex product mixtures via radical decomposition of the chemical initially containing the tertiary amine.

Chemically, tertiary amines are the most commonly used activators of the benzoyl peroxide initiator for curing composite restorative resins and acrylic bone cements. Benzoyl peroxide is also one of the most commonly applied initiators, reacting through a one electron transfer with lower oxidation state metals to initiate polymerization. For example, tertiary amines initiate chemical reactions with benzoyl peroxide resulting in the formation of free radicals capable of initiating polymerization in the curing of the acrylic monomers for bone cements.

In dermatology, the combination of benzoyl peroxide with a tertiary amine has previously been proven useful for treatment of acne. Specifically, the tertiary amine, as chemically present in the drug erythromycin, has been used in consort with benzoyl peroxide, with excellent clinical results. Indeed, clinical trials have shown that the combination of topical erythromycin with benzoyl peroxide is more effective than either the antibiotic or benzoyl peroxide alone for the treatment of acne. The joint treatment of benzoyl peroxide and this tertiary amine also greatly outperforms tretinoin with erythromycin, with clinical differences appearing within 2 weeks of usage.

In conclusion, our data suggests that benzoyl peroxide when used in consort with an allylmine antifungal may be more beneficial than benzoyl peroxide alone for acne vulgaris and warrants further testing. In an era in which physicians are advised to reduce antibiotic prescribing in an attempt to limit the increasing risk of resistance in hospitals and the community, it might be prudent to avoid antibiotics for milder forms of acne and for maintainence therapy, to limit the use of systemic and topical antibiotics for acne to short durations of therapy when necessary, and to seek other treatment modalities. Certainly the combination of benzoyl peroxide and allylamines for treatment of acne warrants further testing.

FIG. 1: Tabulation of patients' accumulated percentage improvement in number of acne comedones, inflamed acne lesions, and degree of facial improvement with Proactiv Solution

|  | Week 2 | Week 4 | Week 6 | Week 8 |
| --- | --- | --- | --- | --- |
| Decrease in # of comedones | 13.3 | 15.1 | 14.4 | 16.3 |
| Decrease in # of inflamed lesions | 26.7 | 26.4 | 31.9 | 33.6 |
| Decrease in degree of facial oiliness | 13.1 | 37.8 | 36.8 | 36.25 |

FIG. 2: Tabulation of patients' accumulated percentage improvement in number of acne comedones, inflamed acne lesions, and degree of facial improvement with the combination of benzoyl peroxide with butenifine

|  | Week 2 | Week 4 | Week 6 | Week 8 |
| --- | --- | --- | --- | --- |
| Decrease in # of comedones | 24.9 | 54.7 | 53.0 | 63.7 |
| Decrease in # of inflamed lesions | 43.6 | 49.0 | 33.5 | 39.4 |
| Decrease in degree of facial oiliness | 29.5 | 39.5 | 46.2 | 51.0 |

FIG. 3: Survey questions posed to study subjects with averages from patient assessment scores with both therapies on the 10-point scale used.

1. How did the treatment perform in reducing the severity of your acne? (1 meaning no improvement, and 10 meaning fabulous improvement)
Proactiv Solution-4.3   benzoyl peroxide/allylamine-7.0
2. How did the treatment perform in reducing the number of acne lesions? (1 meaning no improvement, and 10 meaning did extremely well)
Proactiv Solution-4.3   benzoyl peroxide/allylamine-7.1
3. How did the treatment perform in reducing the amount of redness of acne? (1 meaning no improvement, and 10 meaning did extremely well)
Proactiv Solution-4.3   benzoyl peroxide/allylamine-5.6
4. How easy was the acne treatment to do everyday? (1 meaning very difficult, 10 meaning very easy)
Proactiv Solution-7.5   benzoyl peroxide/allylamine-7.9
5. Does your skin feel softer to you at the completion of the study? (1 meaning much tougher, 5 meaning the same as originally, and 10 meaning much softer)
Proactiv Solution-5.8   benzoyl peroxide/allylamine-6.1
6. Does your skin fell smoother to you at the completion of the study? (1 meaning much rougher, 5 meaning the same as originally, and 10 meaning much smoother)
Proactiv Solution-5.5   benzoyl peroxide/allylamine-6.6
7. Did the product you used seem to prevent breakouts? (1 meaning not at all, and 10 meaning it did a great job)
Proactiv Solution-4.4   benzoyl peroxide/allylamine-6.6
8. How satisfied were you with the treatment? (1 meaning not at all, and 10 meaning very satisfied)
Proactiv Solution-4.5   benzoyl peroxide/allylamine-7.5
9. Would you like to continue the treatment after the study is over? (1 meaning no, and 10 meaning definitely)
Proactiv Solution-5.4   benzoyl peroxide/allylamine-6.6
10. How would you rate your improvement in feeling more comfortable and confident around other people as a result of treatment? (1 meaning no change, and 10 meaning significantly improved)
Proactiv Solution-3.4   benzoyl peroxide/allylamine-5.6

Use of the Composition As a Hospital Cleansing Cream or a Home Cleanser

Benzoyl peroxide and an antibiotic (e.g., clarithromycin) may work against methicillin-resistant *Staphylococcus aureus* and/or vancomycin-resistant *enterococcus* and/or pseudomonas. Preferably, the composition also includes a tertiary amine and/or a transition metal. The produce may be useful as a hospital cleansing cream (for example) in between patients, or as a home cleanser, etc.

Although the invention is discussed primarily in terms of the use of a teriary amine with the benzoyl peroxide, any amine (e.g., a secondary amine) can be used that has the effect of increasing radicals as described above. Tertiary amines are preferred because they are the most active.

What is claimed is:

1. A method of treating a bodily condition comprising topically applying to the body of a human or animal a combination of a peroxide and a tertiary amine, the tertiary amine increasing radicals formed by the peroxide on the body to thereby increase the efficacy of the peroxide in the treatment of the condition, and increasing the potency of the peroxide by at least one of the following steps: (a) combining the peroxide with a material that further increases radicals formed by the peroxide; (b) mixing the peroxide and the tertiary amine after they have been applied to the body; (c) energizing reaction of the peroxide with the tertiary amine on the body; (d) treating the body with an oral or topical anti-oxidant; (e) increasing penetration of the peroxide through a surface of the body; and (f) heating at least one of the peroxide and the tertiary amine before applying them to the body.

2. The method of claim 1 wherein the potency of the peroxide is increased by step (a) which includes combining the peroxide with a base that increases lability of the peroxide.

3. The method of claim 2 wherein the base includes a polar or semipolar solvent.

4. The method of claim 1 wherein the potency of the peroxide is increased by step (a) which includes combining the peroxide with a transition metal.

5. The method of claim 4 wherein at least the transition metal is applied with a device that improves the treatment.

6. The method of claim 1 wherein the potency of the peroxide is increased by step (e) which includes using a film or patch to increase penetration rate of the peroxide through the skin.

7. The method of claim 1 wherein the potency of the peroxide is increased by step (e) which includes encapsulating the peroxide in a vesicle or particle.

8. The method of claim 1 wherein the potency of the peroxide is increased by step (e) which includes physically manipulating the skin to increase its permeability.

9. The method of claim 1 wherein the potency of the peroxide is increased by step (e) which includes electrically manipulating the skin to increase its permeability.

10. The method of claim 1 wherein the potency of the peroxide is increased by step (c) which includes applying heat energy or light energy to the peroxide on the body.

11. The method of claim 1 wherein the peroxide is benzoyl peroxide.

12. A method of killing microorganisms on a surface comprising applying to the microorganisms a combination of a peroxide and a tertiary amine, the tertiary amine increasing radicals formed by the peroxide on the surface to thereby increase the efficacy of the peroxide in killing the microorganisms.

13. The method of claim 12 wherein the surface is the skin, hair, nails, ear, oral mucosa, nasal mucosa, or genital region of a human or animal.

14. The method of claim 12 wherein the surface is the teeth or gums of a human or animal.

15. The method of claim 12 wherein the peroxide and the tertiary amine are included in a cleansing composition for cleaning hard surfaces.

16. The method of claim 12 wherein the peroxide is benzoyl peroxide.

17. A method of preventing or reducing skin aging comprising applying to the skin a combination of a peroxide and a tertiary amine, the tertiary amine increasing radicals formed by the peroxide on the skin to thereby increase the efficacy of the peroxide in preventing or reducing skin aging.

18. The method of claim 17 which prevents or reduces liver spots.

19. The method of claim 17 which additionally comprises applying a transition metal to the skin.

20. The method of claim 17 wherein the peroxide is benzoyl peroxide.

* * * * *